United States Patent [19]

Maddison

[11] Patent Number: 5,388,464
[45] Date of Patent: Feb. 14, 1995

[54] STRESSING DEVICE

[76] Inventor: Anthony Maddison, Stoke Golding Applied Research Laboratory, Willow Park, Upton Lane, Stoke Golding, Nuneaton, Warks, CV13 6EU, England

[21] Appl. No.: 979,865
[22] PCT Filed: Aug. 15, 1991
[86] PCT No.: PCT/GB91/01386
 § 371 Date: Apr. 5, 1993
 § 102(e) Date: Apr. 5, 1993
[87] PCT Pub. No.: WO92/03716
 PCT Pub. Date: Mar. 5, 1992

[30] Foreign Application Priority Data
 Aug. 15, 1990 [GB] United Kingdom ............... 9017887
[51] Int. Cl.⁶ ............................................. G01N 3/02
[52] U.S. Cl. ........................................ 73/856; 73/826
[58] Field of Search ............... 73/856, 826, 827, 808, 73/810, 788, 828, 830, 831, 834, 837

[56] References Cited
U.S. PATENT DOCUMENTS
3,142,980 8/1964 Andersen ........................... 73/837 X
3,433,061 3/1969 Burr .

FOREIGN PATENT DOCUMENTS
0300702 1/1989 European Pat. Off. .
3825657 2/1990 Germany .
4000940 7/1991 Germany ............................ 73/808
60-93941 5/1985 Japan .
1336903 11/1973 United Kingdom ................ 73/826

OTHER PUBLICATIONS
*Soviet Inventions Illustrated*, Week 8710, Abstract KBAV S03 87–071828/10, 18 Mar. 1987, Derwetn Publications Ltd., (London, GB) & SU, A, 1245-926 23 Jul. 1986.

*Primary Examiner*—Hezron E. Williams
*Assistant Examiner*—James M. Olsen
*Attorney, Agent, or Firm*—Webb Ziesenheim Bruening Logsdon Orkin & Hanson

[57] ABSTRACT

The device comprises a tubular body portion (1) in which are fitted first and second jaws (2, 4) for holding a specimen (3) to be tested. A compression spring (5) or pressure chamber (29), are housed within the body portion (1) and act to urge the first jaw (2) outwards whilst the second jaw (4) is secured to the body portion thereby applying stress to the specimen (3). The device is sufficiently small to enable it to be used in confined spaces, such as the underside of a vehicle or within a vehicle engine compartment, so the tests can be carried out in real-life environments. If hydraulic actuation of the pressure chamber (29) is used, varying stresses can be applied to the specimen (3) which are also dependent upon real-life movements and/or stresses.

7 Claims, 2 Drawing Sheets

1

STRESSING DEVICE

This application is a continuation of PCT/GB91/01386 filed Aug. 15, 1991.

TECHNICAL FIELD

This invention relates to a stressing device for use, for instance, in testing the durability of bonded joints.

BACKGROUND ART

The durability of structural adhesive bonds exposed to combinations of stress and an aggresive environment has traditionally been evaluated using large, bulky stressing devices suitable only for use in laboratory based or static outdoor test environments. These devices may typically be a meter or more in length and 5 to 10 cm in width.

DISCLOSURE OF INVENTION

The present invention aims to provide a smaller stressing device suitable for use in confined spaces, e.g. the underside of a vehicle or inside a vehicle engine compartment, to enable durability tests to be conveniently carried out in real-life environments and over extended periods of time.

According to a first aspect of the invention there is provided a stressing device for applying a stress to a specimen being tested, the device comprising a tubular body portion having a bore passing from one end of the device to the other; first and second jaws mounted within the tubular body portion and arranged to be secured to opposite ends of a specimen to be tested; securing means for securing the first jaw to the body portion; and resilient means housed in a chamber within the bore of the body portion and arranged to apply a load to the second jaw and thus to the specimen being tested, at least one cut-out being provided in the side of the body portion to provide access to a specimen held between the first and second jaws and to expose the specimen to the surrounding environment, the device being sufficiently small to enable it to be used in confined spaces, such as the underside of a vehicle or within a vehicle engine compartment, so that tests can be carried out in real-life environments.

According to a second aspect of the invention, there is provided a method of testing a specimen using a stressing device as detailed above comprising the steps of: fitting the specimen within the device and installing the device in a real-life situation, e.g. by mounting it on the body of a vehicle, so it is subject to real-life temperature changes and a real-life chemical environment.

Preferred features of the invention will be apparent from the following description and the subsidiary claims of the specification.

BRIEF DESCRIPTION OF DRAWINGS

The invention will now be further described, merely by way of example, with reference to the accompanying drawings, in which.

BEST MODE OF CARRYING OUT THE INVENTION

Figure 1:
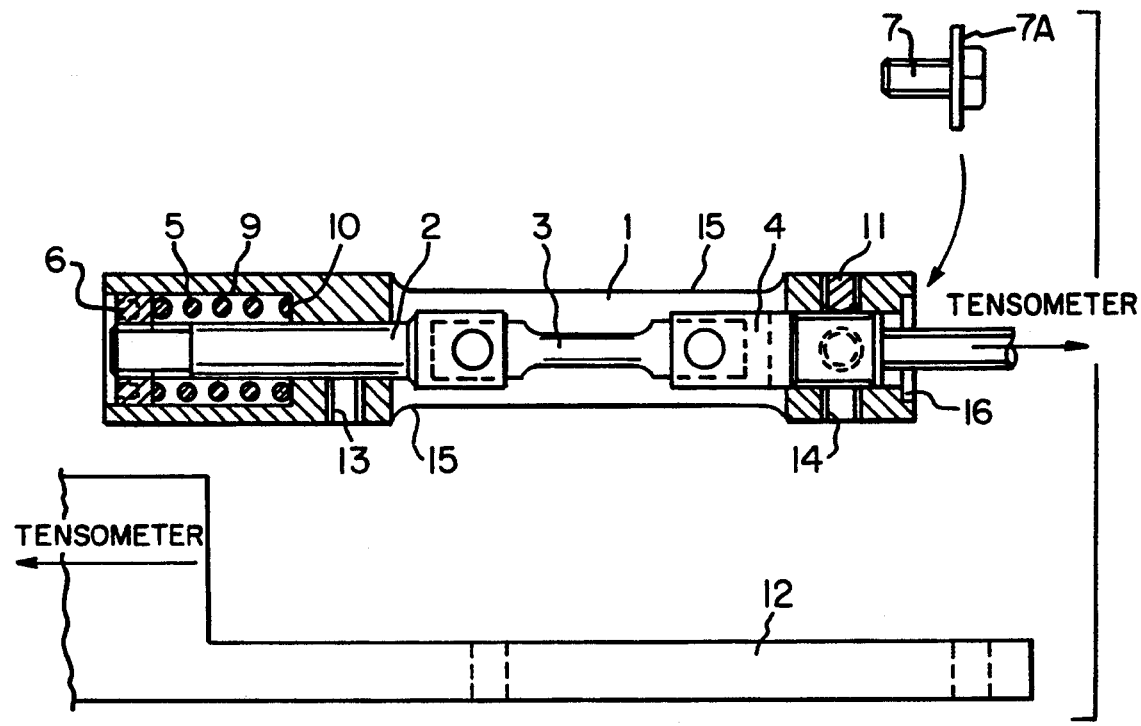
FIG. 1 is a cross-sectional side view of a first embodiment of a stressing device according to the invention and also shows an adaptor for mounting the device within a tensometer.
Figure 2:
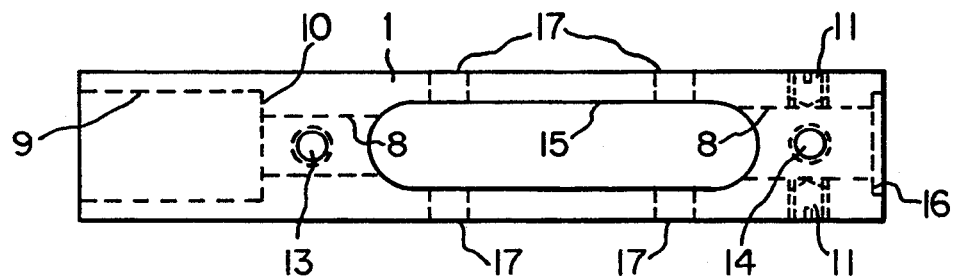
FIG. 2 is a plan view of a body portion of the device shown in FIG. 1.
Figure 3:
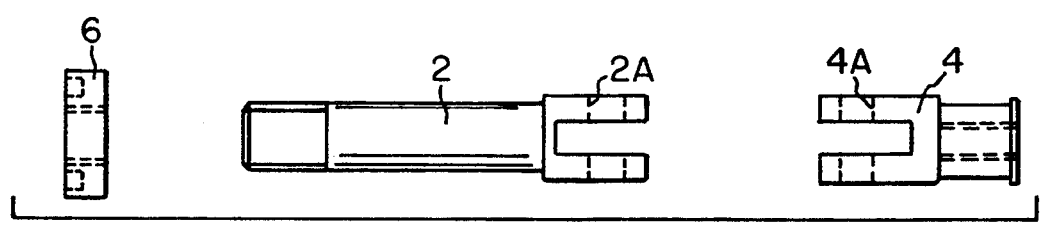
FIG. 3 shows plan views of specimen jaws used in the device shown in FIG. 1 and a nut which fits into one end of the device.

The device illustrated in FIGS. 1 to 3 comprises a substantially tubular body portion 1, a first jaw 2 for holding one end of a specimen 3, a second jaw 4 for holding the other end of the specimen 3, a compression spring 5, a nut 6 which fits into one end of the body portion 1 and a security bolt 7 which fits into the other end of the body portion 1.

In use, the components of the device are assembled as shown in FIG. 1 with the jaws 2 and 4 fitted within a bore 8 of the tubular body portion 1. The specimen 3 is secured between the jaw 2 and 4 by means of stainless steel pins (not shown) fitted through holes 2A and 4A provided in the ends of the jaws 2 and 4. The compression spring 5 is fitted within a spring chamber comprising an enlarged portion 9 of the bore 8 and acts between a shoulder 10 at the inner end of the spring chamber 9 and the nut 6 which is secured to the outer end of the jaw 2. The nut 6 is designed to be a sliding fit within the spring chamber 9 of the bore 8 and is screwed onto the outer end of the jaw 2.

The outer end of the jaw 4 is provided with a threaded fixing for receiving the security bolt 7 and for attaching it to one side of a tensometer (as will be described further below).

The device illustrated in FIGS. 1 to 3 is designed so that a specimen 3 can be accurately stressed without the need to calibrate the spring 5. This is achieved by mounting the device within a conventional tensometer, applying the required stress and then clamping the jaw 4 in place by means of grub screws 11. To do this, the device is first secured to a special adaptor 12 by means of bolts (not shown) secured to holes 13 and 14 provided in the body portion 1. One side of the tensometer is then attached to the adaptor 12 and the other side to the outer end of the jaw 4.

The spring 5 and nut 6 are loosely fitted into the end of the body portion 1 and the tensometer crosshead is then moved until the specimen 3 is approximately centred. The exact load required is then imposed on the specimen 3 by turning the nut 6 and/or moving the tensometer crosshead in such a manner that the specimen 3 remains approximately centered.

The adaptor 12 comprises a rigid bar which is preferably secured to the body portion 1 in two places, i.e. at the holes 13 and 14, to help ensure the device is kept in alignment with the tensometer. The adaptor 12 is designed so that the line between the two sides of the tensometer passes through the center line of the body portion 1 to ensure jaw 4 can freely slide within the body portion 1 as the stress is applied.

As tension is applied between the jaw 4 and the body portion 1, the jaw 4, specimen 3 and jaw 2 are put under tension and the spring 5 is compressed. When the desired stress has been applied, the jaw 4 is locked in position with respect to the body portion 1 by the grub screws 11 so the spring 5 maintains the set stress on the specimen 3. The arrangement shown has four grub screws 11 at right angles to each other, the fourth being fitted into the hole 14 once the adaptor 12 has been disconnected. The grub screws 11 also serve to retain the jaw 4 within the device should the sample 3 fail. The jaw 2 is held captive within the device by the shape of its inner end and the nut 6 secured to its outer end.

Once the desired stress has been set in this way, the device may be removed from the tensometer, detached from the adaptor 12 and the security bolt 7 fitted into the outer end of the jaw 4. The security bolt 7 is provided as a precaution against slippage between the jaw 4 and the grub screws 11 during handling and exposure of the device. The bolt 7 is screwed into the end of the jaw 4 until its flange 7A is seated within a recess 16 provided in the end of the body portion 1. The device can then be mounted in the required environment, e.g. the underside of a vehicle, the holes 13 and 14 being used to secure the device in place.

The tubular body portion 1 may typically be formed from an anodised aluminum alloy (although stainless steel may also be used) and would typically be around 5 to 20 cm in length and have an external diameter of around 1 to 3 cm. The particular device illustrated in FIGS. 1 to 3 is approximately 14 cm long and has an external diameter of approximately 2.5 cm. A large slot 15 or cut-out is provided in one or both sides of the body portion 1 so the sample being tested is exposed to the ambient conditions and is clearly visible. Holes 17 (see FIG. 2) are also provided through the sides of the body portion 1 to facilitate the attachment of a sample 3 to the jaws 2 and 4. The steel pins (not shown) used to attach the sample 3 to the jaws 2 and 4 may be passed through these holes 17 so they can then be fitted into the holes provided in the inner ends of the jaws 2 and 4.

The jaws 2 and 4 may be formed of stainless steel. The inner ends of the jaws 2 and 4 which are attached to the sample being tested may have a variety of forms for securing to a range of different specimen configurations. A number of different forms of jaws may be provided with the device to enable different types of specimens to be held therein.

The jaws 2 and 4 and the corresponding portions of the bore 8 may have a non-circular section, e.g. square or rectangular, to prevent rotation of the jaw 2 and 4 within the body portion 1.

The security nut 7 may also be replaced by some other form of device for preventing movement of the jaw 4 with respect to the body portion 1 once the required load has been applied to the specimen 3, such as an external locking ring (not shown) which screws onto the end of the jaw 4 projecting from the body portion 1 or a transducer (described further below)

During exposure, dimensional changes within the specimen 3 may occur producing corresponding changes in the stress applied thereto. The spring 5 is preferably selected to minimise sensitivity to these dimensional changes and to maximise sensitivity for setting the load by selecting the lightest, i.e. weakest, spring consistent with the load to be applied. Typical spring rates suitable for bonded lap shear joints of aluminium substrates would be around 50–300 N/mm. However, the device can be used with a wide range of spring strengths and is capable of applying very high loads to a sample, e.g. up to 3 KN.

As the spring is encased within the body portion 1, it is reasonably protected from the surrounding environment. However, in some cases, it may be desirable to seal the spring chamber 9 by providing appropriate O-ring seals at each end of the chamber, e.g. in the manner shown in FIG. 5 (described below). Electroless nickel plated springs made of chrome-vanadium steel have been found to be particularly suitable in terms of strength and corrosion resistance.

The assembled device may typically have a weight in the range 50 g to 250 g, for instance around 150 g. This compares with conventional, laboratory stressing devices having a weight of the order of 2 g to 7 kg.

A number of modifications and refinements may be provided for the basic version of the stressing device described above.

Figure 4:
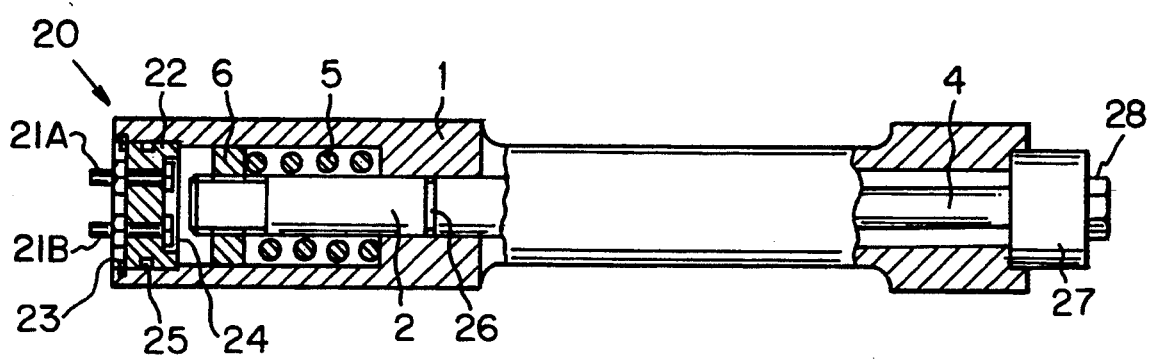
FIG. 4 is a side view of a second embodiment of a stressing device according ot the invention showing two possible modifications to the first embodiment.

As shown in FIG. 4, sensing means may be provided to permit remote detection of failure of the specimen 3 and these are preferably provided within a sealed chamber to protect them from the environment.

In the arrangement illustrated, the sensing means comprises a electrical switch 20 which is normally open but which is closed when the specimen 3 under test fails. The body portion 1 in FIG. 4 is similar to that shown in the preceding Figures but is made slightly longer to accommodate the switch 20. The switch 20 comprises two stainless steel terminals 21A and 21B in the form of small bolts which are mounted in a block 22 of insulating material such as Tufnol (trade name for a fibre reinforced plastics material). The block is mounted within a recess in the end of the body portion 1 and held in place by a circlip 23. A phosphor bronze contact strip 24 is secured to the inner end of one of the terminals 21A and extends across the space between the end of the first jaw 2 and the inner end of the other terminal 21B. If the specimen 3 fails, the first jaw 2 is forced outwards by the pressure of the spring 5 on the nut 6 so the end of the first jaw 2 engages the phosphor bronze contact 24 and pushes this into contact with the terminal 21B thus closing the switch.

The closure of the switch 20 may be sensed by a monitoring device (not shown) remote from the stressing device but electrically connected to the terminals 21A and 21B. A large number of stressing devices, e.g. 100 or 200, mounted on a structure such as a vehicle may all be connected to the same monitoring device and this can be arranged to indicate when any specimen fails and in which device it is fitted.

The switch contacts are housed within the body portion 1 of the device so are protected from the outside environment. However, as additional security, O-ring seals 25 and 26 may be provided between the block 22 and the body portion 1 and between the first jaw 2 and the body portion 1, respectively, as shown to prevent ingress of moisture etc. which might cause the electrical contacts of the switch to corrode.

The arrangement described above provides a simple, robust and compact sensing device. However, other suitable switch arrangements for sensing failure of a specimen will be apparent to those skilled in the art.

FIG. 4 also shows a transducer 27 fitted to the outer end of the second jaw 4. The transducer 27 may comprise strain gauges or other means, e.g. piezoelectric devices, for measuring the stress applied to the specimen 3. With such an arrangement, the grub screws 11 and security bolt 7 are not required to secure the second jaw 4 relative to the body portion 1. Instead, the second jaw 4 is secured to the body portion 1 via the transducer 27. In the arrangement illustrated, a bolt 28 secures the outer end of the second jaw 4 to the transducer 27 which is thus effectively compressed between the bolt 28 and the outer end of the body portion 1 by the stress applied to the specimen 3.

This arrangement is particularly suitable where it is desired to monitor variations in the stress applied to the specimen 3, e.g. due to temperature variations and hence dimensional changes of the specimen or of components of the stressing device. The transducer 27 allows the second jaw 4 to move slightly with respect to the body portion as the stresses vary but these movements will be very small so the second jaw 4 may still be regarded as being effectively secured to the body portion 1.

Various possible constructions for the transducer will be apparent to the person skilled in the art so will not be described. It will also be appreciated that such a transducer may be used with any embodiment of the device, including those shown in the other Figures, and can be used independently of the switch 20 described above.

The transducer may be used for continuous or intermittent monitoring of the stress applied to the specimen and, like the switch 20, may be connected to a remote monitoring device (not shown). It may also be used for measuring the load applied when the device is set up rather than using a tensometer to measure the load as described above.

Figure 5:
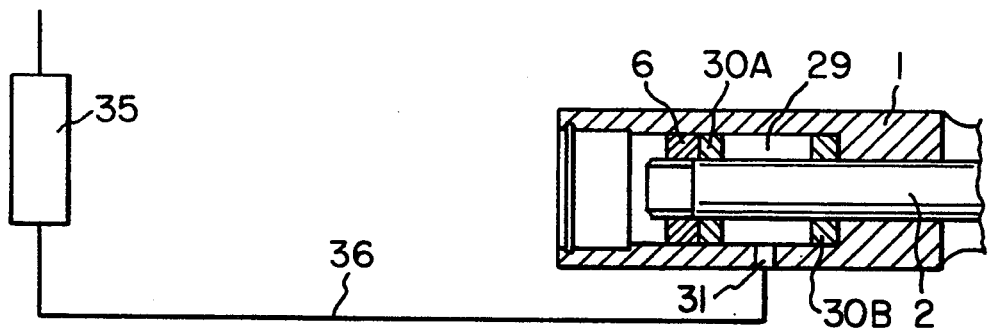
FIG. 5 is a schematic view of one end of a stressing device illustrating a further modification of the embodiments shown in the preceding drawings.

In the arrangement shown in FIG. 5, a pressure chamber 29 is used as the resilient means for applying stress to a specimen 3 in place of the spring 5 (although the resilient means may also comprise a pressure chamber with a compression spring mounted therein).

The pressure chamber 29 is formed within the chamber 9 in the body portion with seals 30A and 30B at each end to seal it from the external environment. Stress is applied to the specimen 3 by pressurising the chamber 29 with hydraulic fluid, via a port 31, from an external source. The pressure within the chamber 29 acts against the seal 30A to urge the nut 6 and hence the first jaw 2 outwards in the same manner as the compression spring described in the earlier embodiments. Other arrangements for sealing the chamber 29 will be apparent to those skilled in the art. The pressure chamber may also be in the form of a double acting piston arrangement so both compressive and tansile stresses can be applied to the specimen 3.

One benefit of stressing the specimen in this way is that the pressure within the chamber 29 can be arranged to vary in dependence upon real-life conditions such as the movements of a vehicle to which the device is attached. Pressure may, for instance, be applied to the chamber 29, via hydraulic lines and the port 31, by a movement or stress sensor which senses movements or stresses applied to a structure.

Cyclic stresses may thus be applied to the specimen 3 and these may vary randomly in dependence upon movements or oscillations of real-life conditions experienced by a structure, such as a vehicle body, as it is used. The pressure in the chamber 29 may vary from zero (or even negative pressures) up to 1000 psi (6900 KN/m$^2$) or even up to 2000 psi (13.8 KN/m$^2$).

Figure 6A:
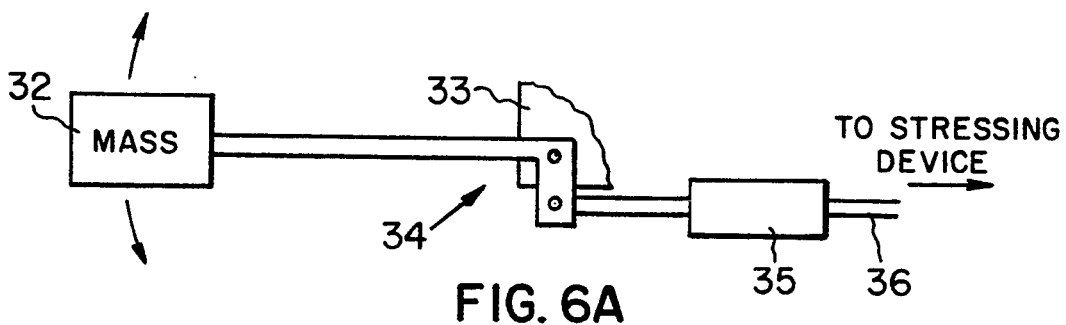
FIGS. 6A and 6B are schematic diagrams of two forms of movement sensor which may be used in conjunction with the device shown in FIG. 5.
Figure 6B:
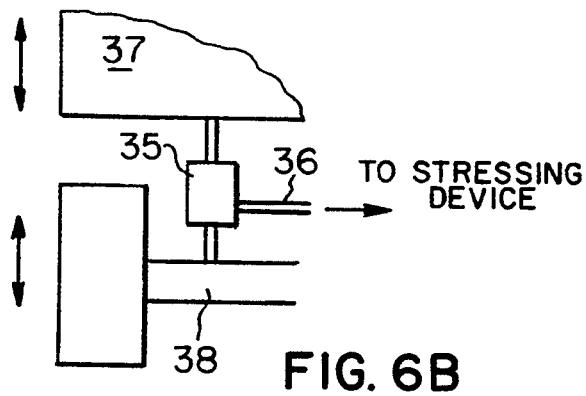

FIGS. 6A and 6B illustrate two forms of a movement sensor which may be used to actuate the hydraulic pressure chamber 29.

In FIG. 6A a vertically oscillating mass 32 is pivotably mounted to a structure 33 such as a vehicle body so as to be free to oscillate vertically in dependence upon the vehicle movements. Vertical oscillation of the mass 32 is transferred by a lever mechanism 34 to movement of a piston within a hydraulic master cylinder or hydraulic pressure intensifier 35. Movement of the piston and the action of the master cylinder or pressure intensifier 35 produces pressure variations in a hydraulic pipe 36 which can be connected to the port 31 of one or more stressing devices.

In FIG. 6B, a master cylinder or pressure intensifier 35 is connected between a vehicle body 37 and a wheel axle 38 so as to sense directly the relative movement of the axle 38 with respect to the body 37. Again, the pressure variations produced are transmitted to the pressure chamber 29 of one or more stressing devices by a hydraulic pipe 36.

A wide variety of other sensors for sensing the movement or stresses applied to a structure and providing a pressure signal to the stressing device which varies in dependence upon these real-life variations can, of course, be used in place of those described above. The system may also be refined, as desired, by the use of pressure intensifiers and/or by buffering or damping the pressure variations depending on the requirements of the test. If the stressing device were used in the laboratory, these might, for instance, include arrangements employing motor driven cams and pistons etc.

It will be appreciated that very small volume changes of within the pressure chamber 29 are required to produce relatively large changes in the stress applied to a specimen 4 held within the device. With the appropriate use of pressure intensifiers, it is therefore feasible to use a single movement or stress sensor to provide the same varying pressure signals to a large number of stressing devices.

So, by using hydraulic activation, it is possible to apply the same variable stresses to a large number of specimens. A single source of hydraulic pressure may, for instance, be applied to the pressure chambers of one hundred or more stressing devices, either in the field or in the laboratory, so that the specimen mounted in each device experiences the same stresses. This would be very difficult to achieve using any other arrangement, e.g. mechanical system transferring varying loads by means of cams, levers, pistons etc.

A transducer such as that described in relation to FIG. 4 may, of course, be used to measure and monitor the stress applied to the specimen in a device using hydraulic actuating means as described above.

In addition to the modifications described above, an extensometer may also be incorporated in the device for creep observations.

It may also be desirable to use an anti-galvanic arrangement in which the sample 3 is electronically isolated from the remainder of the device and from the structure on which the device is mounted, e.g. by the use of appropriate insulating inserts and bushes.

As mentioned above, the device is designed to be very small and lightweight so it can be used in natural environments where space is limited and without major inconvenience. It is particularly suitable for mounting on the underside of a vehicle, e.g. for testing the durability of bonded joints, and in such a situation it may need to be left in place for at least a year so that the sample is exposed to the full cycle of weather and environmental conditions in spring, summer, autumn and winter.

With the arrangements described in FIGS. 1 to 3, the required stress can be pre-set in the laboratory using a conventional tensometer. The test loads can thus be accurately set and checked. This avoids the need to calibrate the spring of each individual device. However, the spring may still be calibrated in the conventional manner should this be desired. A transducer such as that described in relation to FIG. 4 may be used to measure the applied stress in other arrangements.

The device has a wide range of possible applications, including:
adhesive bond durability testing
stress corrosion studies on metals
creep studies, e.g. of metals, polymers and composites
environmental stress-cracking of polymers It is difficult to simulate real-life environments in the laboratory and the stressing device described above helps overcome this. First, it is small enough to be conveniently used in real-life situations, e.g. attached to the body of a vehicle, so it is exposed to the same environment as the vehicle, i.e. it experiences the same temperature changes and chemical environment (rain etc.). In addition, with the arrangement shown in FIG. 5, rather than applying a fixed, pre-set stress to the specimen, it can be subjected to varying stresses which are dependent upon the randomly varying stresses experienced by the structure on which the device is mounted.

Although designed for use in the field, the device may also be used in the laboratory where its small size enables the cabinet space required for multiple tests to be greatly reduced compared to conventional devices. Its simple structure and design also enable it to be considerably less expensive to manufacture than conventional devices.

The device described above is designed to be of simple construction with as few parts as necessary. The body portion 1 is shaped to house all the necessary components and is provided with the appropriate recesses, bores and holes to hold the components accurately in place. This integrated design of the body portion 1 enables the device to be made much smaller than conventional stressing devices and with the minimum number of components.

Despite its small size, the device can however be used for the majority of stress tests conventionally carried out. The device is capable of holding a British Standard lap joint which is 1 inch (2.54 cm) wide with a ½ inch (1.25 cm) overlap (although it may be necessary to reduce the length of the sample).

As indicated above, the device can be modified or adapted in a variety of ways so despite its simplicity it is also very versatile.

The device is designed mainly to house single samples rather than a plurality of samples connected in series as used in conventional devices. However, it is in many cases more convenient to use a plurality of such small devices each housing a single sample rather than one large device housing a plurality of samples. A plurality of small samples may, nevertheless, be connected in series and housed within the illustrated device if desired.

INDUSTRIAL APPLICABILITY

The stressing device may be manufactured and used in a wide variety of tests in which a specimen is to be stressed, whether in the laboratory or in real-life situations.

I claim:

1. A stressing device for applying a stress to a specimen being tested, the device comprising:
   a tubular body portion having a bore passing from one end of the device to the other;
   first and second jaws mounted within the tubular body portion and arranged to be secured to opposite ends of a specimen to be tested;
   securing means for securing the first jaw to the body portion; and
   resilient means housed in a chamber within the bore of the body portion and arranged to apply a load to the second jaw and thus to the specimen being tested,
   wherein at least one cut-out is provided in the side of the body portion to provide access to a specimen held between the first and second jaws and to expose the specimen to the surrounding environment, and wherein further the first and second jaws are shaped and are provided with attachments such that, once assembled within the body portion, they are held captive and cannot become separated from the body portion, even when a specimen fails, without removing the said attachments, the device being sufficiently small to enable it to be used in confined spaces so that tests can be carried out in real-life environments.

2. A device as claimed in claim 1 in which the securing means comprises at least one bolt for rigidly securing the second jaw relative to the body portion.

3. A device as claimed in claim 1 in which the resilient means comprises a compression spring, said stressing device further comprising a means for mounting said stressing device within a conventional tensometer which can apply a pre-set load to the specimen such that the securing means can secure the second jaw relative to the body portion so as to maintain the load on the specimen when the device is removed from the tensometer.

4. A device as claimed in claim 1 in which the resilient means comprises a pressure chamber connected by a hydraulic pipe to a movement or stress sensor arranged to provide varying pressures within the hydraulic pipe in dependence upon movement or stresses experienced by a structure to which the movement or stress sensor is mounted.

5. A device as claimed in claim 1 in which the resilient means comprises a compression spring, whereby the resilient means acts between the body portion and attachment means attached to the outer end of the second jaw so as to apply tension to a specimen held between the first and second jaws.

6. A method of testing a specimen using a stressing device as claimed in claim 1 comprising the steps of: fitting the specimen within the device and installing the device in a real-life situation so it is subjected to real-life temperature changes and a real-life chemical environment.

7. A method as claimed in claim 6 in which varying stresses are applied to the specimen by hydraulic pressure means within the device, the hydraulic pressure means being actuated by movement sensing means subject to real-life movements, whereby the stresses applied to the specimen vary in dependence upon the real-life movements experienced by the sensing means.

* * * * *